United States Patent
Im et al.

(10) Patent No.: US 6,800,479 B2
(45) Date of Patent: Oct. 5, 2004

(54) RECOMBINANT ADENOVIRUSES EXPRESSING INTERLEUKIN-18 PROTEIN AND GENE THERAPY USING THEM

(75) Inventors: Dong-Soo Im, Taejeon (KR); Won-Kyung Cho, Taejeon (KR); Kyung-Sun Hwang, Taejeon (JP)

(73) Assignees: Samyang Genex Corporation, Seoul (KR); Korea Research Institute of Bioscience & Biotechnology, Taejon (KR)

( * ) Notice: Subject to any disclaimer, the term of this patent is extended or adjusted under 35 U.S.C. 154(b) by 0 days.

(21) Appl. No.: 10/105,080

(22) Filed: Mar. 22, 2002

(65) Prior Publication Data

US 2003/0143203 A1 Jul. 31, 2003

(30) Foreign Application Priority Data

Dec. 11, 2001 (KR) ........................................ 2001-78296

(51) Int. Cl.$^7$ ...................... C12N 15/24; C12N 15/861; A61K 48/00
(52) U.S. Cl. .................... 435/320.1; 435/455; 435/456; 424/93.2; 514/44
(58) Field of Search ............................. 435/320.1, 455, 435/456; 424/93.2; 514/44

(56) References Cited

U.S. PATENT DOCUMENTS 6,060,283 A * 5/2000 Okura et al. ............. 435/69.52

OTHER PUBLICATIONS

Osaki et al. "Potent antitumor effects and mediated by local expression of the mature form of the interferon-gamma inducing factor, interleukin-18 (IL-18)," Gene Ther. 6 (5): 808-815, May 1999.*

Mountain, Andrew, "Gene therapy: the first decade", *Trends in Biotechnology*, vol. 18, pp. 119-128 (Mar. 2000).

Micallef, Mark J., et al., "Interleukin 18 Induces the Sequential Activation of Natural Killer Cells and Cytotoxic T Lymphocytes to Protect Syngeneic Mice from Transplantation with Meth A Sarcoma", *Cancer Research*, vol. 57, pp. 4557-4563 (Oct. 15, 1997).

Kyung-Sun Hwang, et al., "The Antitumor Effects of the Recombinant Adenoviruses Encoding IL-18 Mutants in Murine Tumor Model", *Proceedings of the American Association for Cancer Research*, vol. 42, No. 2444, pp. 454-455, plus 20 pages from a slide presentation (Mar. 2001).

Dinarello, Charles A., et al., "Overview of interleukin-18: more than an interferon-β inducing factor", *Journal of Leukocyte Biology*, vol. 63, pp. 658-664 (Jun. 1998).

Gennaro, Alfonso R. ed., *Remington's Pharmaceutical Sciences*, 18th Edition, Mack Publishing Company, Chapters 83, 84, and 85, pp. xv, xvi, and 1519-1580 (1990).

* cited by examiner

*Primary Examiner*—Scott D. Priebe
(74) *Attorney, Agent, or Firm*—Ladas & Parry

(57) ABSTRACT

The present invention relates to recombinant adenoviruses expressing interleukin-18 protein, and gene therapy using them. More particularly, the invention provides recombinant adenoviruses Ad.promIL-18, Ad.GMmIL-18, Ad.prohIL-18, Ad.hIL-18CPP32- and Ad.preprotrypsin.hIL-18CPP32- which are effectively capable of treating a variety of cancer cells by promoting and enhancing an immune response in vivo.

13 Claims, 11 Drawing Sheets

SEQUENCE LISTING

<160> NUMBER OF SEQ ID NOS: 16

<210> SEQ ID NO 1
<211> LENGTH: 474
<212> TYPE: DNA
<213> ORGANISM: Human mature interleukin-18 gene

<400> SEQUENCE: 1

```
tactttggca agcttgaatc taaattatca gtcataagaa atttgaatga ccaagttctc      60
ttcattgacc aaggaaatcg gcctctattt gaagatatga ctgattctga ctgtagagat     120
aatgcacccc ggaccatatt tattataagt atgtataaag atagccagcc tagaggtatg     180
gctgtaacta tctctgtgaa gtgtgagaaa atttcaactc tctcctgtga gaacaaaatt     240
```

-continued

```
atttccttta aggaaatgaa tcctcctgat aacatcaagg atacaaaaag tgacatcata      300
ttctttcaga gaagtgtccc aggacatgat aataagatgc aatttgaatc ttcatcatac      360
gaaggatact ttctagcttg tgaaaaagag agagaccttt ttaaactcat tttgaaaaaa      420
gaggatgaat tggggatag  atctataatg ttcactgttc aaaacgaaga ctag            474
```

<210> SEQ ID NO 2
<211> LENGTH: 474
<212> TYPE: DNA
<213> ORGANISM: mouse mature interleukin-18 gene

<400> SEQUENCE: 2

```
aactttggcc gacttcactg tacaaccgca gtaatacgga atataaatga ccaagttctc       60
ttcgttgaca aaagacagcc tgtgttcgag gatatgactg atattgatca aagtgccagt      120
gaacccagac ccagactgat aatatacatg tacaaagaca gtgaagtaag aggactggct      180
gtgaccctct ctgtgaagga tagtaaaatg tctaccctct cctgtaagaa caagatcatt      240
tcctttgagg aaatggatcc acctgaaaat attgatgata tacaaagtga tctcatattc      300
tttcagaaac gtgttccagg acacaacaag atggagtttg aatcttcact gtatgaagga      360
cactttcttg cttgccaaaa ggaagatgat gctttcaaac tcattctgaa aaaaaggat       420 gaaaatgggg ataaatctgt aatgttcact ctcactaact tacatcaaag ttag            474
```

<210> SEQ ID NO 3
<211> LENGTH: 52
<212> TYPE: DNA
<213> ORGANISM: GM-CSF secretion signal

<400> SEQUENCE: 3

```
gatgtggctg cagaatttac ttttcctggg cattgtggtc tacagcctct ca              52
```

<210> SEQ ID NO 4
<211> LENGTH: 193
<212> TYPE: PRT
<213> ORGANISM: Human interleukin-18 precursor mutant

<400> SEQUENCE: 4

```
Met Ala Ala Glu Pro Val Glu Asp Asn Cys Ile Asn Phe Val Ala Met
 1               5                  10                  15

Lys Phe Ile Asp Asn Thr Leu Tyr Phe Ile Ala Glu Asp Asp Glu Asn
                20                  25                  30

Leu Glu Ser Asp Tyr Phe Gly Lys Leu Glu Ser Lys Leu Ser Val Ile
            35                  40                  45

Arg Asn Leu Asn Asp Gln Val Leu Phe Ile Asp Gln Gly Asn Arg Pro
        50                  55                  60

Leu Phe Glu Asp Met Thr Glu Ser Asp Cys Arg Glu Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
```

-continued

```
                145                 150                 155                 160
Leu Ala Cys Glu Lys Glu Arg Asp Leu Phe Lys Leu Ile Leu Lys Lys
                    165                 170                 175
Glu Asp Glu Leu Gly Asp Arg Ser Ile Met Phe Thr Val Gln Asn Glu
                180                 185                 190
Asp

<210> SEQ ID NO 5
<211> LENGTH: 192
<212> TYPE: PRT
<213> ORGANISM: mouse interleukin-18 precursor mutant

<400> SEQUENCE: 5

Met Ala Ala Met Ser Glu Asp Ser Cys Val Asn Phe Lys Glu Met Met
  1               5                  10                  15
Phe Ile Asp Asn Thr Leu Tyr Phe Ile Pro Glu Glu Asn Gly Asp Leu
                 20                  25                  30
Glu Ser Asp Asn Phe Gly Arg Leu His Cys Thr Thr Ala Val Ile Arg
             35                  40                  45
Asn Ile Asn Asp Gln Val Leu Phe Val Asp Lys Arg Gln Pro Val Phe
         50                  55                  60
Glu Asp Met Thr Glu Ile Asp Gln Ser Ala Ser Glu Pro Gln Thr Arg
 65                  70                  75                  80
Leu Ile Ile Tyr Met Tyr Lys Asp Ser Glu Val Arg Gly Leu Ala Val
                 85                  90                  95
Thr Leu Ser Val Lys Asp Ser Lys Met Ser Thr Leu Ser Cys Lys Asn
                100                 105                 110
Lys Ile Ile Ser Phe Glu Glu Met Asp Pro Pro Glu Asn Ile Asp Asp
            115                 120                 125
Ile Gln Ser Asp Leu Ile Phe Phe Gln Lys Arg Val Pro Gly His Asn
        130                 135                 140
Lys Met Glu Phe Glu Ser Ser Leu Tyr Glu Gly His Phe Leu Ala Cys
145                 150                 155                 160
Gln Lys Glu Asp Asp Ala Phe Lys Leu Ile Leu Lys Lys Lys Asp Glu
                165                 170                 175
Asn Gly Asp Lys Ser Val Met Phe Thr Leu Thr Asn Leu His Gln Ser
            180                 185                 190

<210> SEQ ID NO 6
<211> LENGTH: 582
<212> TYPE: DNA
<213> ORGANISM: Human interleukin-18 precursor mutant

<400> SEQUENCE: 6
atggctgctg aaccagtaga agacaattgc atcaactttg tggcaatgaa atttattgac     60
aatacgcttt actttatagc tgaagatgat gaaaacctgg aatcagatta ctttggcaag    120
cttgaatcta aattatcagt cataagaaat ttgaatgacc aagttctctt cattgaccaa    180
ggaaatcggc ctctatttga agatatgact gagtctgact gtagagagaa tgcaccccgg    240
accatattta ttataagtat gtataaagat agccagccta gaggtatggc tgtaactatc    300
tctgtgaagt gtgagaaaat ttcaactctc tcctgtgaga acaaaattat ttcctttaag    360
gaaatgaatc ctcctgataa catcaaggat acaaaaagtg acatcatatt ctttcagaga    420
agtgtcccag acatgataa taagatgcaa tttgaatctt catcatacga aggatacttt    480
ctagcttgtg aaaaagagag agacctttttt aaactcattt tgaaaaaaga ggatgaattg    540
```

```
ggggatagat ctataatgtt cactgttcaa acgaagact ag                582
```

<210> SEQ ID NO 7
<211> LENGTH: 579
<212> TYPE: DNA
<213> ORGANISM: Mouse interleukin-18 precursor mutant

<400> SEQUENCE: 7

```
atggctgcca tgtcagaaga ctcttgcgtc aacttcaagg aaatgatgtt tattgacaac    60
acgctttact ttatacctga agaaaatgga gacctggaat cagacaactt tggccgactt   120
cactgtacaa ccgcagtaat acggaatata atgaccaag ttctcttcgt tgacaaaaga   180
cagcctgtgt tcgaggatat gactgagatt gatcaaagtg ccagtgaacc ccagaccaga   240
ctgataatat acatgtacaa agacagtgaa gtaagaggac tggctgtgac cctctctgtg   300
aaggatagta aatgtctac cctctcctgt aagaacaaga tcatttcctt tgaggaaatg   360
gatccacctg aaaatattga tgatatacaa agtgatctca tattctttca gaaacgtgtt   420
ccaggacaca acaagatgga gtttgaatct tcactgtatg aaggacactt tcttgcttgc   480
caaaaggaag atgatgcttt caaactcatt ctgaaaaaaa aggatgaaaa tgggdataaa   540
tctgtaatgt tcactctcac taacttacat caaagttag                          579
```

<210> SEQ ID NO 8
<211> LENGTH: 474
<212> TYPE: DNA
<213> ORGANISM: Human mature interleukin-18 mutant

<400> SEQUENCE: 8

```
tactttggca agcttgaatc taaattatca gtcataagaa atttgaatga ccaagttctc    60
ttcattgacc aaggaaatcg gcctctattt gaagatatga ctgagtctga ctgtagagag   120
aatgcacccc ggaccatatt tattataagt atgtataaag atagccagcc tagaggtatg   180
gctgtaacta ctctctgtga agtgtgagaaa atttcaactc tctcctgtga gaacaaaatt   240
atttccttta ggaaatgaa tcctcctgat aacatcaagg atacaaaaag tgacatcata   300
ttctttcaga aagtgtcccc aggacatgat aataagatgc aatttgaatc ttcatcatac   360
gaaggatact tctagcttg tgaaaaagag agagaccttt ttaaactcat ttgaaaaaa   420
gaggatgaat ggggggatag atctataatg ttcactgttc aaaacgaaga ctag          474
```

<210> SEQ ID NO 9
<211> LENGTH: 474
<212> TYPE: DNA
<213> ORGANISM: Mouse mature interleukin-18 mutant

<400> SEQUENCE: 9

```
aactttggcc gacttcactg tacaaccgca gtaatacgga atataaatga ccaagttctc    60
ttcgttgaca aagacagcc tgtgttcgag gatatgactg atattgatca aagtgccagt   120
gaacccaga ccagactgat aatatacatg tacaaagaca gtgaagtaag aggactggct   180
gtgaccctct ctgtgaagga tagtaaaatg tctaccctct cctgtaagaa caagatcatt   240
tcctttgagg aaatggatcc acctgaaaat attgatgata caaagtga tctcatattc   300
tttcagaaac gtgttccagg acacaacaag atggagtttg aatcttcact gtatgaagga   360
cactttcttg cttgccaaaa ggaagatgat gctttcaaac tcattctgaa aaaaaggat   420
gaaaatgggg ataaatctgt aatgttcact ctcactaact tacatcaaag ttag          474
```

```
<210> SEQ ID NO 10
<211> LENGTH: 157
<212> TYPE: PRT
<213> ORGANISM: Human mature inerleukin-18 mutant

<400> SEQUENCE: 10

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
                20                  25                  30

Met Thr Glu Ser Asp Cys Arg Glu Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 11
<211> LENGTH: 157
<212> TYPE: PRT
<213> ORGANISM: Mouse mature inerleukin-18 mutant

<400> SEQUENCE: 11

Asn Phe Gly Arg Leu His Cys Thr Thr Ala Val Ile Arg Asn Ile Asn
 1               5                  10                  15

Asp Gln Val Leu Phe Val Asp Lys Arg Gln Pro Val Phe Glu Asp Met
                20                  25                  30

Thr Asp Ile Asp Gln Ser Ala Ser Glu Pro Gln Thr Arg Leu Ile Ile
            35                  40                  45

Tyr Met Tyr Lys Asp Ser Glu Val Arg Gly Leu Ala Val Thr Leu Ser
        50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155

<210> SEQ ID NO 12
<211> LENGTH: 26
```

-continued

```
<212> TYPE: DNA
<213> ORGANISM: Artificial Sequence
<220> FEATURE:
<223> OTHER INFORMATION: primer for mouse interleukin-18 gene

<400> SEQUENCE: 12
gaacaatggc tgccatgtca gaagac                                      26

<210> SEQ ID NO 13
<211> LENGTH: 26
<212> TYPE: DNA
<213> ORGANISM: Artificial Sequence
<220> FEATURE:
<223> OTHER INFORMATION: primer for mouse interleukin-18 gene

<400> SEQUENCE: 13
acctggcttt gatgtaagtt agtgag                                      26

<210> SEQ ID NO 14
<211> LENGTH: 28
<212> TYPE: DNA
<213> ORGANISM: Artificial Sequence
<220> FEATURE:
<223> OTHER INFORMATION: primer for human interleukin-18 gene

<400> SEQUENCE: 14
caggaattca agatggatgc tgaaccag                                    28

<210> SEQ ID NO 15
<211> LENGTH: 28
<212> TYPE: DNA
<213> ORGANISM: Artificial Sequence
<220> FEATURE:
<223> OTHER INFORMATION: primer for human interleukin-18 gene

<400> SEQUENCE: 15
gaactgcaga ctagtcttcg ttttgaac                                    28

<210> SEQ ID NO 16
<211> LENGTH: 45
<212> TYPE: DNA
<213> ORGANISM: extracellular secretion signal of preprotrypsin

<400> SEQUENCE: 16
atgtctgcac ttctgatcct agctcttgtt ggagctgcag ttgct                 45
```

RECOMBINANT ADENOVIRUSES EXPRESSING INTERLEUKIN-18 PROTEIN AND GENE THERAPY USING THEM

CROSS REFERENCE TO RELATED APPLICATION

This application is based on application No 10-2001-78296 filed in the Korean Industrial Property Office on Dec. 11, 2001, the content of which is incorporated hereinto by reference.

BACKGROUND OF THE INVENTION (a) Field of the Invention

The present invention relates to recombinant adenoviruses expressing interleukin-18 proteins, and gene therapy using them. More particularly, the invention relates to a method of treating cancer cells by delivering the recombinant adenoviruses expressing interleukin-18 to cancer cells and inducing an immune response against tumor cells.

(b) Description of the Related Art

Cancer treatment is mostly carried out by surgical operation, irradiation, treatment using chemicals, methods using an immune promoting agent, etc. However, due to frequent recurrence and several side effects, more efficient and safer therapy has been required.

Due to the recent development of gene manipulation techniques, gene therapy using endogenous genes has been spotlighted in treating several congenital intractable diseases, as well as cancers. Gene therapy is a technique of treating diseases with proteins that are endogenously produced by injecting genes into cells and expressing them after the examination of molecular biological and biochemical causes of diseases. Gene therapy was attempted for the first time by the French Anderson group in America in September 1990, by introducing a gene into a patient suffering from combined immunodeficiency syndrome, and since then, more than 2,500 patients have been subjected to clinical trials.

For effective application of gene therapy to a cancer, the selection of therapeutic genes and vectors enabling selective and specific delivery to affected cells is important. Until now, the thymidine kinase of the herpes simplex virus, the cytosine deaminase of E.coli, p53, TRAIL (TNF-related apoptosis-inducing ligand), a gene for inhibiting angiogenesis, etc. have been used as therapeutic genes. As vectors, adenovirus, adeno-associated virus, retrovirus, liposome, and the like are used. However, those vectors are actually delivered to only a small portion of cancer cells when applied, and consequently, only a small portion of cancer cells express the therapeutic genes, and thus the efficiency of remedy is not that high (Mountain A, *Trends in Biotechnology* 18: 119–128, 2000).

If cytokines, immune response promoting factors, are used to remove tumors, they can induce a tumor-specific cellular immune response. In this case, even though therapeutic genes are introduced to a part of tumor cells, more effective remedy is possible because induction and systemic circulation of tumor-specific cytotoxic-T lymphocytes which causes the removal of tumor cells at distant site in which the therapeutic genes are not introduced.

Interleukin-18 (IL-18) is an immune response promoting factor, and it has also been known as interferon gamma inducing factor (IGIF). Interleukin-18 increases the cytotoxicity of T cells and NK cells, proliferates activated T cells, and stimulates Th1 cells to produce interleukin-2 and interferon-γ (Dinarello C. A. et al., *Methods* 63:658–644, 1998). Also, it inhibits the synthesis of IgE by inducing interferon gamma from B cells, increases the production of granulocyte-macrophage colony stimulating factor (hereinafter referred to as 'GM-CSF'), and promotes the production of interleukin-2. In addition, it inhibits the production of interleukin-10, an immune suppressing cytokine.

Interleukin-18 is synthesized as a precursor in a biologically inactive state, and then cleaved with interleukin-1β-converting enzyme (ICE, caspase-1), a cysteine protease present in the cells, to be converted into an active form. The precursor or activated mature interleukin-18 is digested with caspase-3 (CPP32) and is thus inactivated.

The gene of interleukin-18 has been isolated from humans (GenBank accession number E17135) and mice (GenBank accession number E17139) and recently, anticancer efficiency tests wherein interleukin-18 proteins are administered directly into mice have been attempted, and it has been reported that they exhibit effects to some degree. It is believed that interferon gamma produced from T cells or activated NK cells have a key role in those effects (Micallef et al. Cancer Research 57, 4557–4563, 1997). Accordingly, if in the invention, interleukin-18 is injected into cancer cells as a DNA and not a protein, by adenoviral vectors enabling its overexpression it is expected that more effective anticancer treatment can be achieved.

SUMMARY OF THE INVENTION

It is an object of the invention to provide an interleukin-18 protein mutant that has the interferon gamma inducing ability and is not inactivated by caspase-3.

It is a further object of the invention to provide a gene encoding an interleukin-18 protein mutant that has the interferon gamma inducing-ability and is not inactivated by caspase-3.

It is a further object of the invention to provide a method enabling an interleukin-18 protein to be extracellularly expressed.

It is a further object of the invention to provide a method enabling an interleukin-18 protein to be expressed in tumor cells.

It is a further object of the invention to provide a vector capable of expressing an interleukin-18 protein and a mutant interleukin-18 protein.

It is a further object of the invention to provide a recombinant virus capable of expressing an interleukin-18 protein and a mutant interleukin-18 protein.

It is a further object of the invention to provide a method of treating tumor cells using a recombinant adenovirus expressing interleukin-18.

To accomplish the aforementioned objects, the invention provides an interleukin-18 protein wherein a cleavage site for caspase-3 is substituted by an amino acid selected from the group consisting of alanine, arginine, asparagine, cysteine, glutamine, glutamic acid, glycine, histidine, isoleucine, leucine, lysine, methionine, phenylalanine, proline, serine, threonine, tryptophan, tyrosine, and valine.

Also, the invention provides an interleukin-18 gene comprising a nucleotide sequence encoding the interleukin-18 protein.

Also, the invention provides a recombinant adenovirus comprising (a) a promoter operably linked to an interleukin-18 gene so that it can be expressed, (b) the interleukin-18 gene, and (c) a polyadenylation signal sequence.

Also, the invention provides a method for inhibiting the proliferation of tumor cells by injecting the recombinant adenovirus into cells and expressing the recombinant interleukin-18 protein.

Also, the invention provides a method of expressing an interleukin-18 protein capable of inhibiting the proliferation of tumor cells and enhancing an immune response, and of secreting it extracellularly.

DETAILED DESCRIPTION OF THE PRESENT INVENTION

Figure 1A:
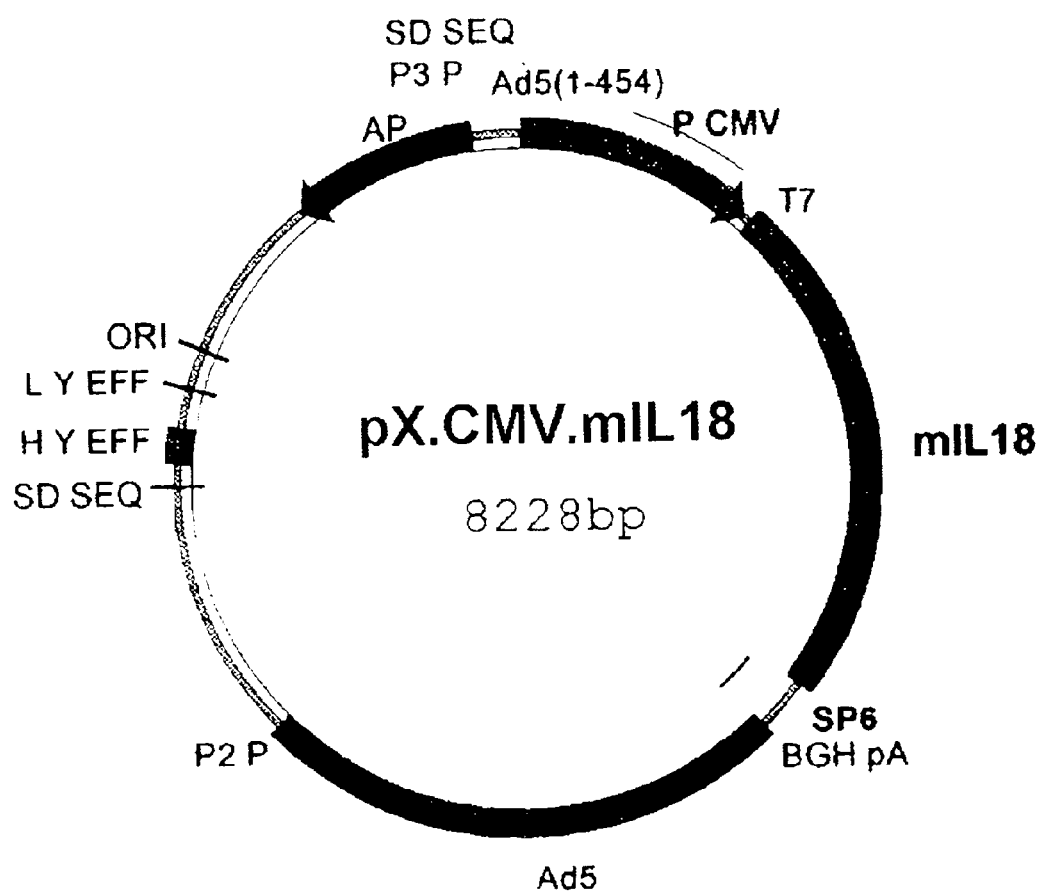
FIGS. 1a-1d represent the gene map of recombinant vectors pX.dCMV.mIL-18, pX.dCMV.GMmIL-18, pX.dCMV.hIL-18, and pX.dCMV.hIL-18CPP32-.
Figure 1B:
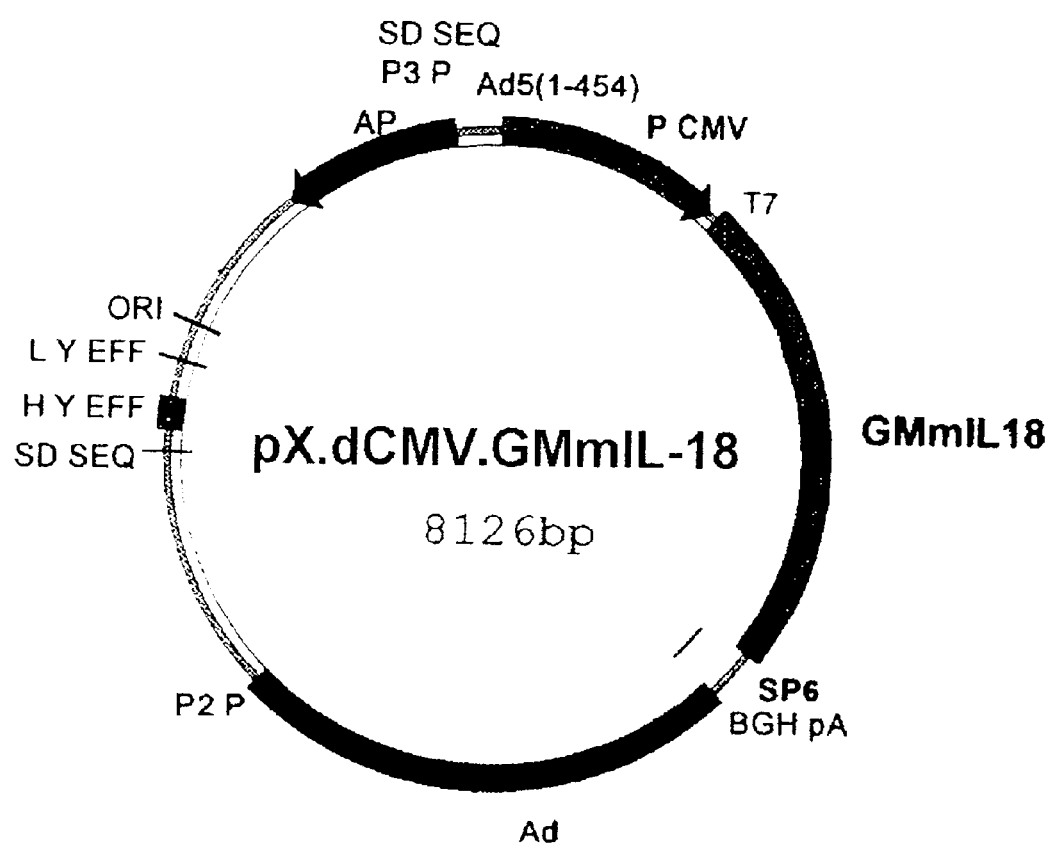
Figure 1C:
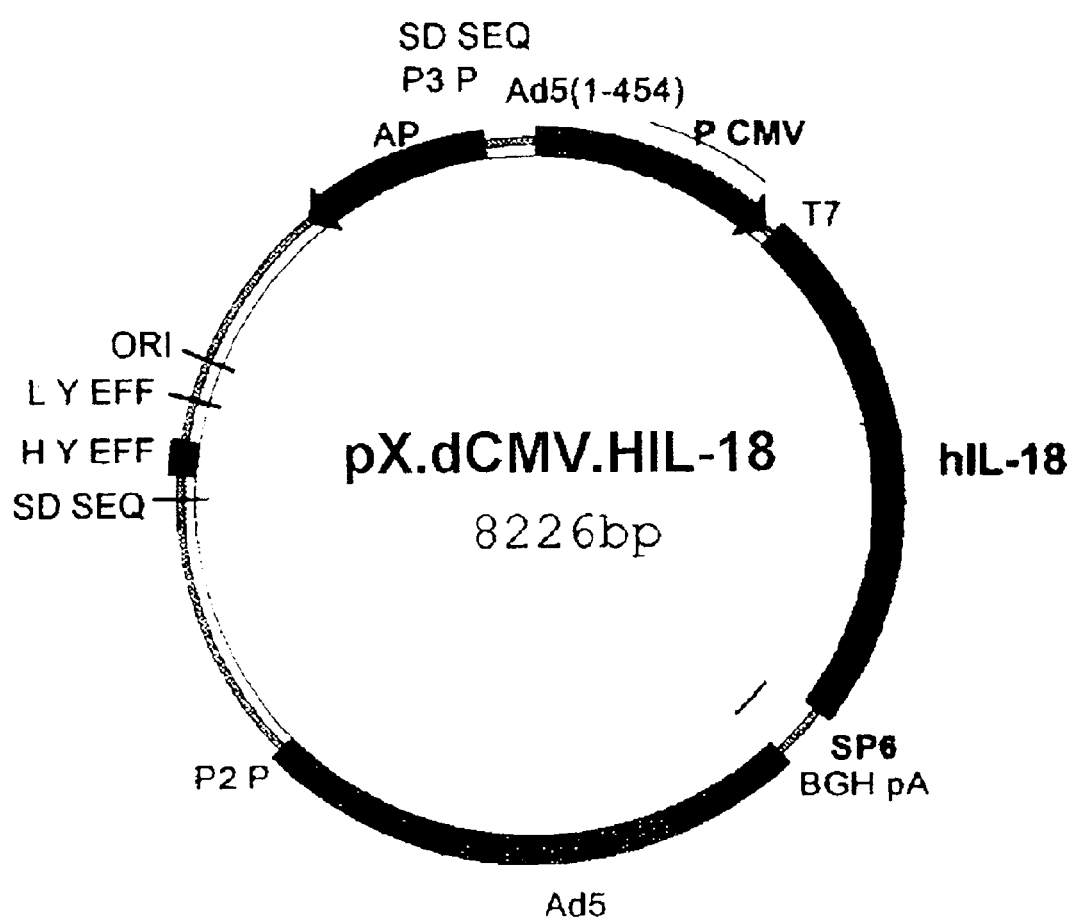
Figure 1D:
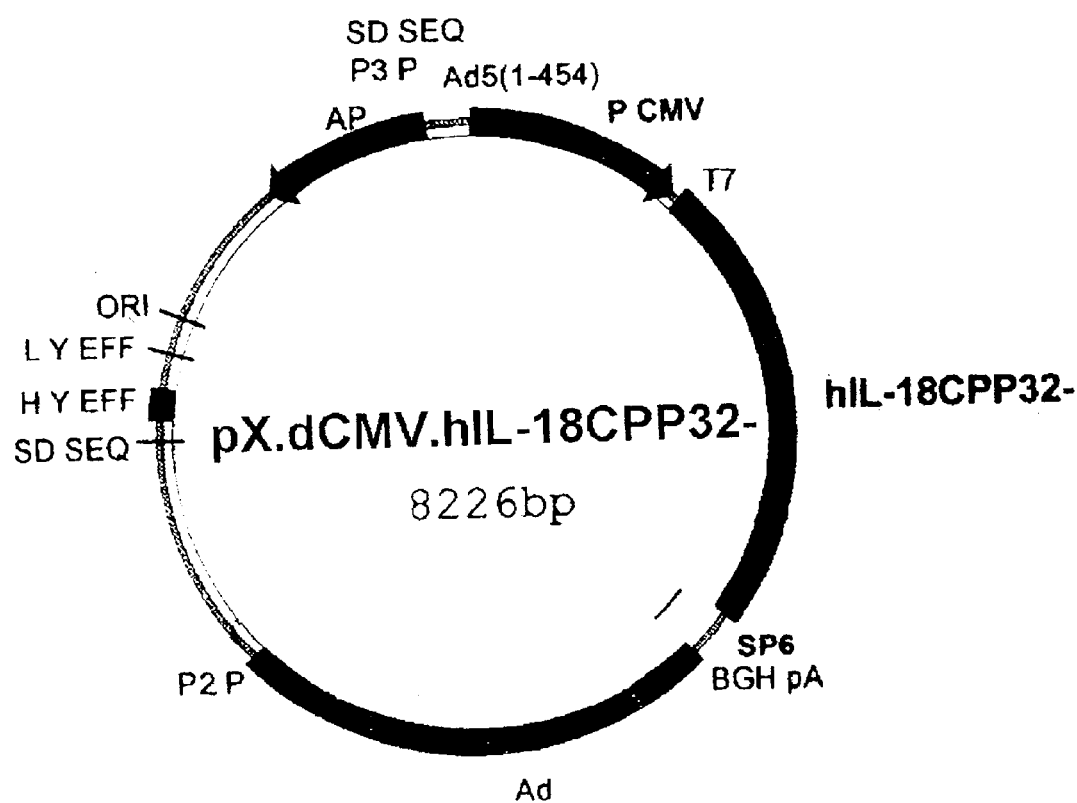

Interleukin-18 protein is a cytokine functioning in the growth, differentiation, and activity of immune cells. The interleukin-18 gene is expressed as a precursor (pro-interleukin-18 polypeptide), and it becomes a mature interleukin-18 protein by the removal of its N-terminal sequence by caspase-1. The mature interleukin-18 proteins have an activity functioning as cytokine. Then, precursors or mature interleukin-18 proteins are inactivated by the cleavage of the downstream of aspartic acid residues by caspase-3. Hence, IL-18 mutants that are not digested with caspase-3 can be designed to increase the half-life of interleukin-18 proteins in tumor cells in which caspase-3 exists or can be activated. Also, interleukin-18 proteins that express extracellularly can be designed so as to generate the immune boosting effects of interleukin-18 toward tumor cells in which interleukin-18 proteins are not expressed.

The intereleukin-18 proteins referred to herein are those possessing the activity of interleukin-18 proteins, preferably a wild-type interleukin-18 protein precursor and its mutants, or a wild-type mature interleukin-18 protein and its mutants. Interleukin-18 genes comprise a wild-type interleukin-18 gene precursor and its mutants, or a wild-type mature interleukin-18 gene and its mutants, and they further comprise a sequence for extracellular secretion.

In the present invention, interleukin-18 protein mutants having interferon gamma induction ability and that are not inactivated by caspase-3 are prepared. These mutants are prepared by substituting an amino acid sequence at the position cleaved with caspase-3 by an amino acid selected from the group consisting of alanine, arginine, asparagine, cysteine, glutamine, glutamic acid, glycine, histidine, isoleucine, leucine, lysine, methionine, phenylalanine, proline, serine, threonine, tryptophan, tyrosine, and valine. It is desirable that the substituted amino acid does not suppress the activity of a mature interleukin-18 protein, and it is preferably glutamic acid.

The cleavage site for caspase-3 is aspartic acid at position 71 or 76 of human interleukin-18 protein (Gene Bank NO. Q14116). The cleavage site for caspase-3 in murine interleukin-18 protein (Gene Bank No. NP-032386) is aspartic acid at position 69.

Preferred interleukin-18 protein mutants are the proteins of SEQ ID NO:4, SEQ ID NO:5, SEQ ID NO:10, or SEQ ID NO:11. SEQ ID NO:4 is a mutant of human interleukin-18 precursor protein wherein amino acids at positions 71 and 76 of the interleukin-18 protein are substituted by glutamic acid, and SEQ ID NO:5 is a mutant of murine interleukin-18 precursor protein wherein an amino acid at position 69 of the interleukin-18 protein is substituted by glutamic acid. SEQ ID NO:10 is the amino acid sequence of the mutant of human mature interleukin-18 protein, and SEQ ID NO:11 is the amino acid sequence of the mutant of murine mature interleukin-18 protein.

Such interleukin-18 protein mutants are not digested with caspase-3 in cells, and they have long-term activity, thereby being effective in inhibiting tumor proliferation.

In addition, mutant genes encoding the interleukin-18 protein mutants are prepared. These mutant genes comprise nucleotide sequences encoding the interleukin-18 protein, wherein an amino acid sequence at the position cleaved with caspase-3 is substituted by an amino acid selected from the group consisting of alanine, arginine, asparagine, cysteine, glutamine, glutamic acid, glycine, histidine, isoleucine, leucine, lysine, methionine, phenylalanine, proline, serine, threonine, tryptophan, tyrosine, and valine.

Preferred mutant genes are polynucleotides comprising nucleotide sequences encoding the protein selected from the group consisting of SEQ ID:4, SEQ ID NO:5, SEQ ID NO:10, and SEQ ID NO:11. Examples of the mutant genes are the polynucleotides of SEQ ID NO:6, SEQ ID NO:7, SEQ ID NO:8, and SEQ ID NO:9.

Also, in the invention, to increase the extracellular secretion of interleukin-18 proteins, nucleotides comprising interleukin-18 gene sequences and extracellular signal sequences are prepared. Preferably, the nucleotides are those comprising a signal sequence of granulocyte-macrophage colony stimulating factor (GM-CSF) or preprotrypsin at the 5' terminal of the nucleotide sequences, encoding mature interleukin-18 protein or mature interleukin-18 protein mutant. An example of the signal sequence is the nucleotide sequence of SEQ ID NO:3 and SEQ ID NO:16.

More preferably, interleukin-18 gene sequences are the nucleotide sequence of SEQ ID NO:1, the nucleotide sequence of SEQ ID NO:2, nucleotide sequences encoding the protein of SEQ ID NO:10, or nucleotide sequences encoding the protein of SEQ ID NO:11. An example of the nucleotide sequences of the protein of SEQ ID NO:10 is SEQ ID NO:8, and an example of the nucleotide sequences encoding the protein of SEQ ID NO:11 is SEQ ID NO:9.

Further, recombinant adenoviruses expressing the interleukin-18 protein or its mutants can be prepared.

First, recombinant adenoviral transfer vectors comprising constructs capable of expressing an interleukin protein or its mutants are prepared. The adenoviral transfer vectors are those capable of transferring specific genes to adenoviruses by homologous recombination.

The constructs comprise a promoter, a gene encoding the interleukin-18 protein or its mutants, and a polyadenylation signal.

As promoters, CMV (Cytomegalovirus)-derived promoter, LTRs of Rous Sarcoma Virus, LTRs of mouse Leukemia virus, Simian Virus early or late promoter, or interleukin-18 promoter can be used, and preferably, the CMV-derived promoter is used.

The interleukin-18 gene includes an interleukin-18 precursor, a mature interleukin-18 gene, an interleukin-18 precursor mutant, or a mature interleukin-18 mutant.

The adenoviral transfer vectors comprising the mature interleukin-18 gene or mature interleukin-18 mutant may further comprise a transcription initiation codon (ATG).

The Interleukin-18 mutant genes for the interleukin-18 precursor mutants and mature interleukin-18 mutants comprise nucleotide sequences encoding the interleukin-18 protein mutants wherein an amino acid sequence at the position cleaved with caspase-3 is substituted by an amino acid selected from the group consisting of alanine, arginine, asparagine, cysteine, glutamine, glutamic acid, glycine, histidine, isoleucine, leucine, lysine, methionine, phenylalanine, proline, serine, threonine, tryptophan, tyrosine, and valine.

The interleukin-18 genes may further comprise a secretion signal sequence enabling the recombinant proteins to be extracellularly secreted. All sequences known heretofore as a secretion signal sequence can be preferably used, and most preferably, the signal sequence of a GM-CSF(SEQ ID NO:3) or preprotrypsin(SEQ ID NO:16) is used.

Examples of the prepared recombinant adenoviral transfer vectors are pX.dCMV.mIL-18, pX.dCMV.hIL-18, pX.dCMV.GMmIL-18, pX.dCMV.hIL-18CPP32-, and pX.preprotrypsin.hIL-18CPP32-. The structures of pX.dCMV.mIL-18, pX.dCMV.hIL-18, pX.dCMV.GMmIL-18, and pX.dCMV.hIL-18CPP32- are shown in FIGS. 1a-1d.

The recombinant adenoviral transfer vectors are infected into cells together with adenoviral parental vectors, and they transfer the interleukin-18 expression constructs (promoter—interleukin-18 gene—transcription terminator) of the transfer vectors into the parental vectors. The transfer of the interleukin-18 expression constructs is carried out by homologous recombination between a portion of the adenovirus genes of the recombinant vector and the parental vectors containing the same, and this is simply represented in FIG. 2.

Examples of the adenoviral parental vectors are pBHG10 and pJM17.

The recombinant adenoviruses of the invention comprise a promoter, an interleukin-18 gene, and a polyadenylation signal sequence added to the adenoviral parental vector. Preferred recombinant adenoviruses are Ad.promIL-18, Ad.GMmIL-18, Ad.prohIL-18, Ad.hIL-18CPP32-, and Ad.preprotrypsin.hIL-18CPP32-.

Ad.promIL-18 comprises a murine wild-type interleukin-18 gene, and Ad.GMmIL-18 comprises a GM-CSF signal sequence (SEQ ID NO:3) and a murine mature interleukin-18 gene (SEQ ID NO:2). Ad.prohIL-18 comprises a human wild-type interleukin-18 gene, and Ad.hIL-18CPP32-, which has a substitution at the position of interleukin-18 protein to be cleaved with caspase-3, and comprises SEQ ID NO:6. Ad.preprotrypsin.hIL-18CPP32- comprises a preprotrypsin (SEQ ID NO:16) and SEQ ID NO:6.

Also, Ad.preprotrysin.hIL-18CPP32- comprises a human mature interleukin-18 gene (SEQ ID NO:1) and a preprotrypsin signal sequence (SEQ ID NO:16), and it can produce the mature human interleukin protein (SEQ ID NO:10) which is not digested with caspase-3 and is extracellularly secreted.

Ad.GMmIL-18 is designated as Ad.IL-18, and it was deposited on Aug. 31, 2001 under KCTC10062BP.

As the recombinant adenoviruses of the invention lack an E1 gene which is essential for the proliferation of adenoviruses, they cannot replicate and propagate when introduced into cancer cells, whereas they express a large quantity of interleukin-18 proteins under the control of a CMV promoter and secrete them extracellularly.

When the recombinant adenoviruses are infected into Hela cells, the expressed IL-18 proteins are detected both intracellularly and extracellularly.

Figure 4:
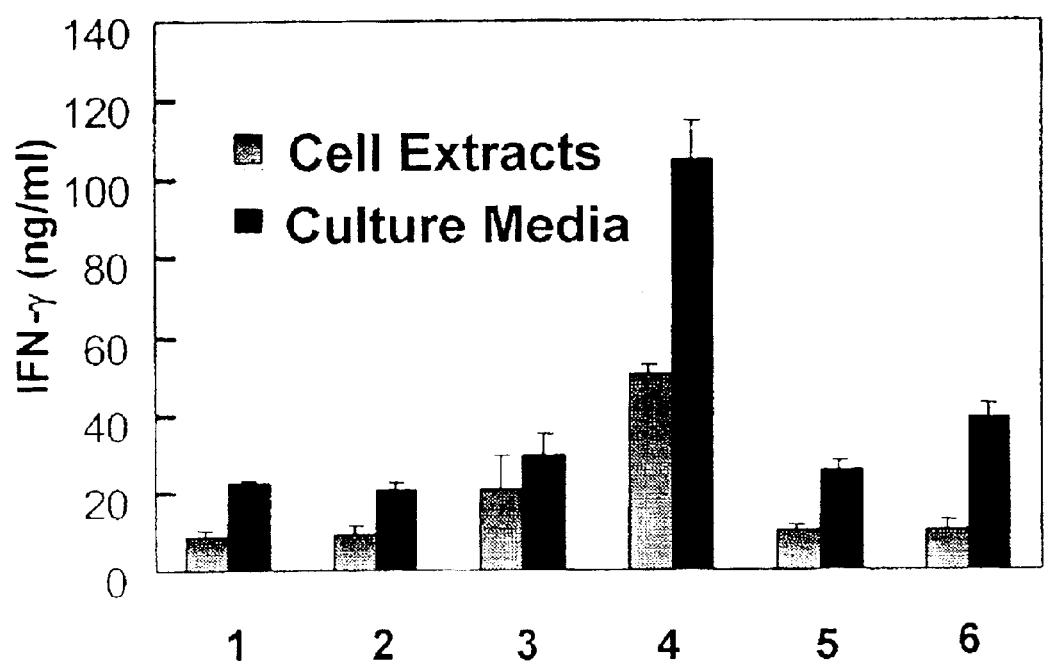
FIG. 4 shows the amount of interferon gamma production by recombinant interleukin-18 proteins measured by the ELISA method.

Also, the recombinant interleukin-18 proteins expressed by the recombinant adenoviruses of the invention have a physiological activity. As interleukin-18 is an inducing factor of interferon gamma, the production of interferon gamma can be observed from the culture medium of spleen cells excised from mice when the spleen cells are treated with the protein extracts and culture medium obtained from cells infected with the recombinant adenoviruses constructed in the invention. As a result, Ad.promIL-18, Ad.GMmIL-18, Ad.prohIL-18, and Ad.hIL-18CPP32- all increase the production of interferon gamma, and especially Ad.GMmIL-18, which secretes the recombinant interleukin-18 proteins extracellularly, and induces interferon gamma in the largest quantities (FIG. 4). Thus, it implies that the extracellular secretion signal increases the effect of interleukin-18 protein as a cytokine.

The recombinant interleukin-18 proteins expressed in the recombinant adenoviral transfer vectors or the recombinant adenoviruses of the invention are isolated and purified by conventional methods, and can be used as an immune enhancing composition.

Also, the invention provides compositions comprising recombinant adenoviruses. Preferred recombinant adenoviruses are at least one selected from the group of Ad.promIL-18, Ad.GMmIL-18, Ad.prohIL-18, Ad.hIL-18CPP32-, and Ad.preprotrypsin.hIL-18CPP32-. Ad.promIL-18, Ad.prohIL-18, or Ad.hIL-18CPP32- can be administrated together with Ad.ICE. Ad.ICE is a recombinant adenovirus expressing caspase-1, which removes the pro site from the recombinant protein expressed in the form of pro-interleukin-18, and generates a mature interleukin-18 protein.

The compositions may further include one or more acceptable pharmacological compositions. The pharmacological compositions are vehicles or diluents, and they are at least one selected from the group consisting of saline, buffered saline, dextrose, water, glycerol, and ethanol. However, the vehicles and diluents are not limited thereto. Suitable preparations known in the relevant art are described in the literature (Remington's Pharmaceutical Science (recent version), Mack Publishing Company, Easton Pa.).

The compositions can be used orally or parenterally, preferably being used in an injectable form. For example, they can be administered into tumor cells by single intratumoral injection. The dosage of the composition is the one commonly used for gene therapy of tumors using adenoviral vectors, and the maximum is to inject $1 \times 10^{12} - 10^{13}$ of recombinant adenovirus particles. However, the dosage is not limited thereto. It is desirable that the exact dosage is applied differently, depending on the condition of patients, the kind of diseases, medicines to be co-administered, etc., and such dosage is determined through pre-clinical and clinical stage 1.

Also, the invention provides a method for enhancing the immune response or inhibiting the proliferation of tumor cells by the compositions comprising the said recombinant adenoviruses.

The recombinant adenoviruses can be used for the purpose of enhancing immune response, and they can be executed especially for all kinds of cancers, for example, for kidney cancers, liver cancers, head and neck cancer, skin cancers, stomach cancers, breast cancers, etc.

The recombinant adenoviruses of the invention are replication defective but capable of expressing a large quantity of interleukin-18 proteins and extracellularly secreting them when delivered to tumor cells, and the overexpressed interleukin-18 proteins function as a cytokine, inducing a cellular immune response, thereby enhancing NK cells activity and also inducing a specific cytotoxic T-lymphocytes against tumor cells.

Figure 5:
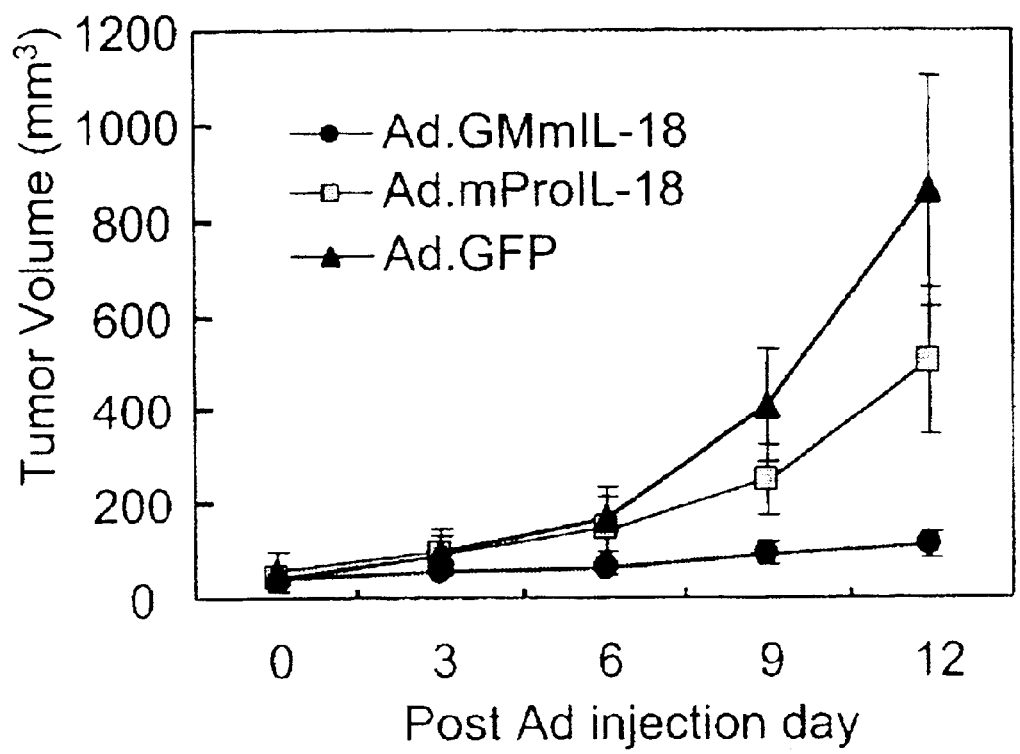
FIG. 5 is a graph showing the degree of proliferation inhibition in mouse kidney cancer tumor cells measured after the administration of Ad.GMmIL-18.
Figure 6:
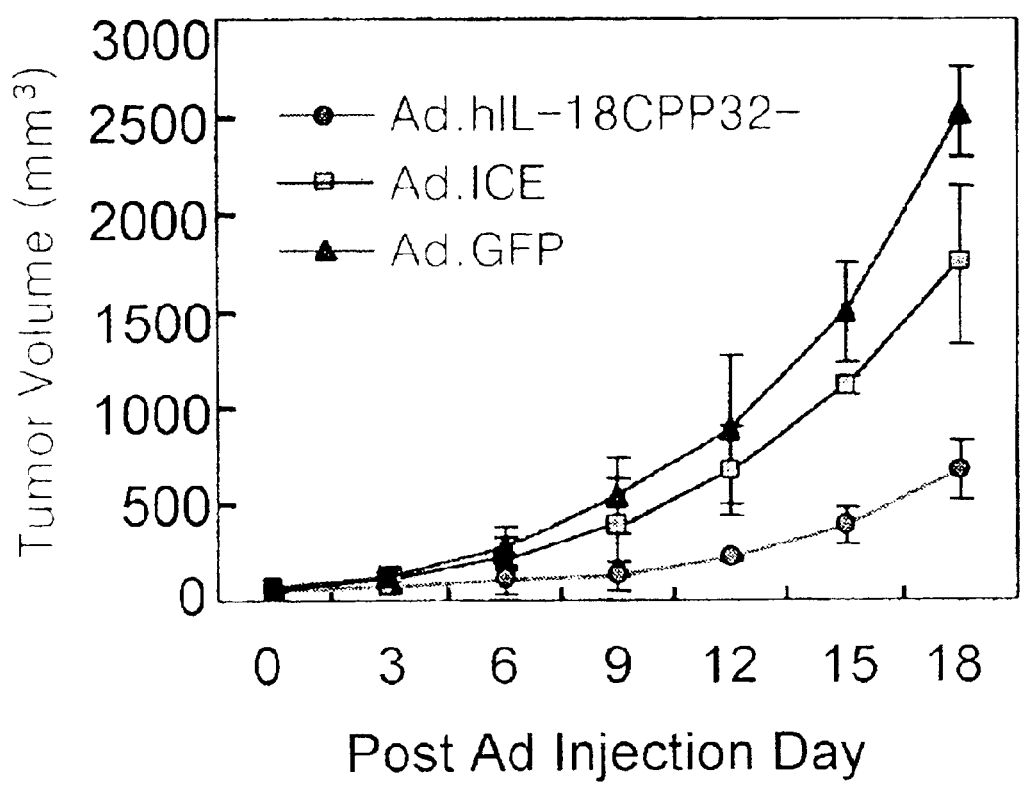
FIG. 6 is a graph showing the proliferation suppression of tumor cells measured after the co-administration of Ad.hIL-18CPP32- and Ad.ICE into a liver cancer mouse model.
Figure 7:
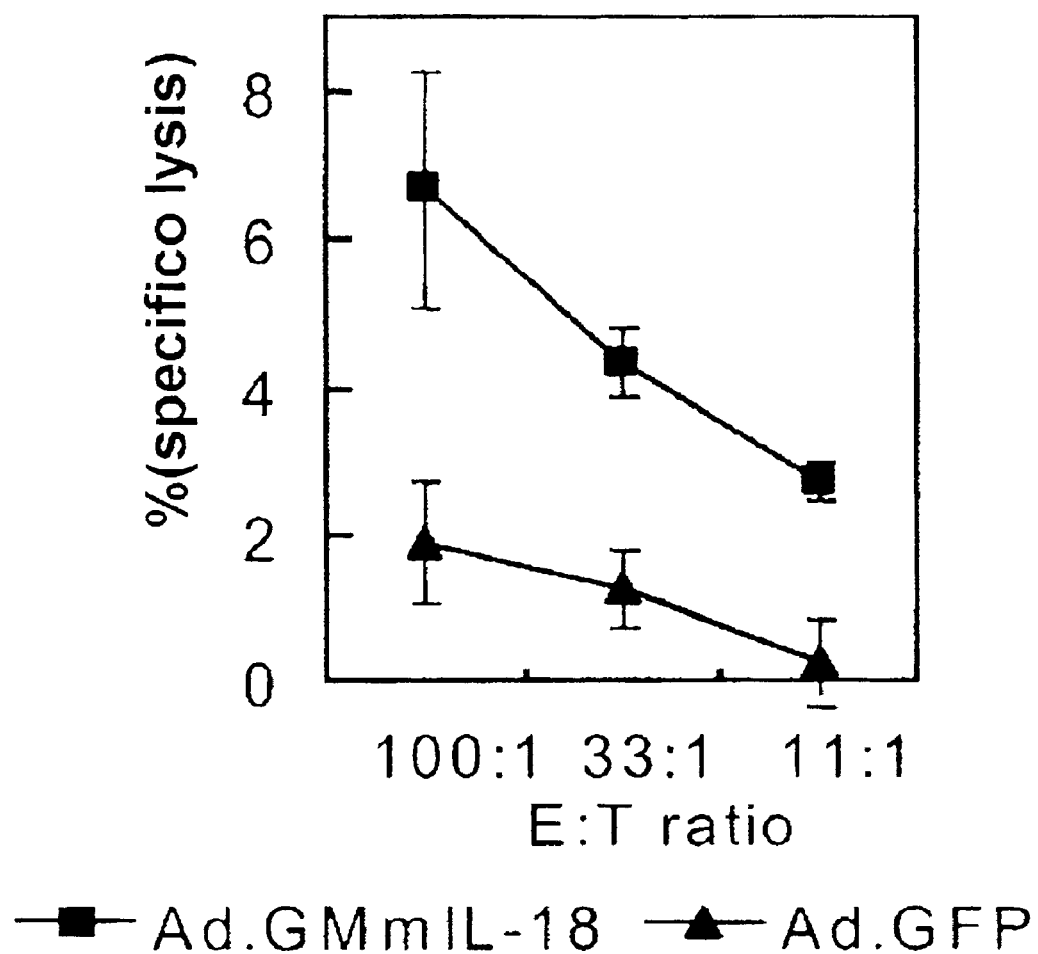
FIG. 7 is a graph showing the induction of cytotoxic lymphocytes specific to tumor cells by the interleukin-18 proteins produced from Ad.GMmIL-18.
Figure 8:
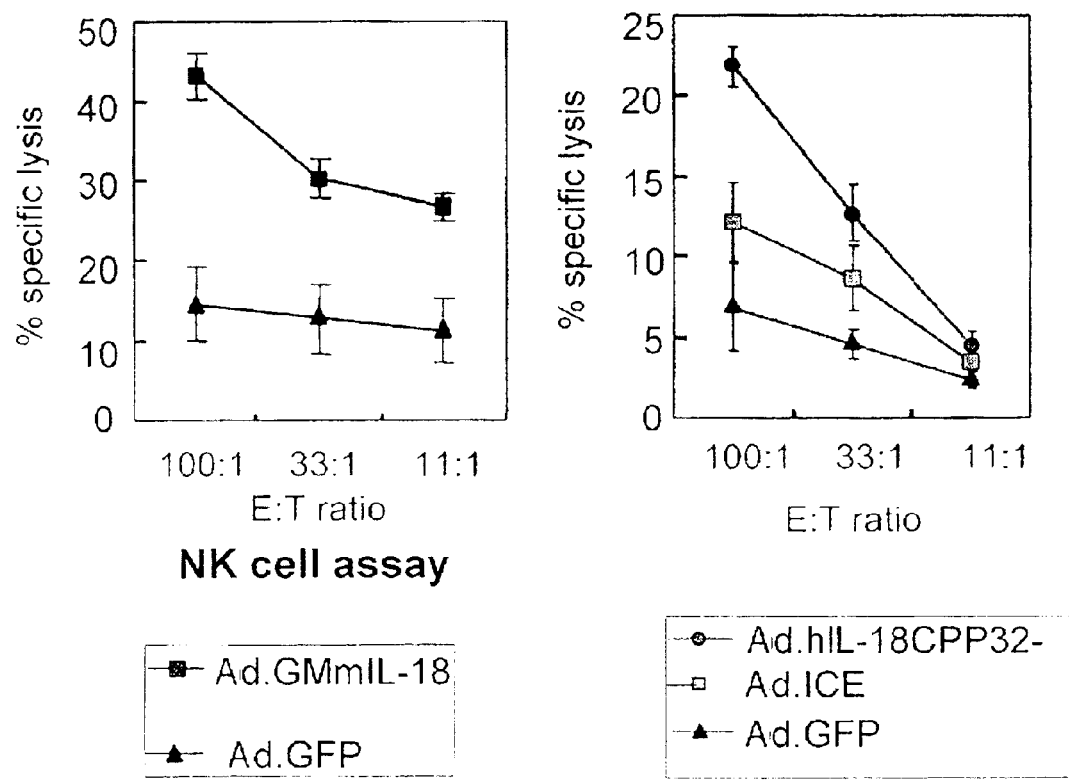
FIG. 8 is a graph showing the enhancement in the activity of natural killer cells by the interleukin-18 proteins produced from Ad.GMmIL-18 and Ad.hIL-18CPP32-.

It was found in the invention that the treatment of tumor cells with the recombinant adenoviruses inhibits the proliferation of tumors (FIG. 5 and FIG. 6). Especially, Ad.GMmIL-18 exhibits stronger anticancer effect than Ad.promIL-18, and from this, it is inferred that the extracellular secretion of interleukin-18 is important in anticancer effects. Also, it was observed that the treatment of mice having tumors with Ad.promIL-18, Ad.GMmIL-18, and Ad.ICE+Ad.hIL-18CPP32-, respectively, increases the cytotoxicity of cancer cell specific T lymphocytes, induces a Th1 cytokine, and increases the activity of NK cells (FIG. 7 and FIG. 8).

The following describes the examples of the invention. The following examples are to illustrate the invention, and it should be understood that the invention is not limited to the following examples.

EXAMPLE 1

Cloning of Interleukin-18 Gene (1) Cloning of Murine Interleukin-18 Gene

RAW cells, mouse macrophages, were cultured, and RT-PCR was carried out using the set of primers of SEQ ID NO:12 and SEQ ID NO:13 to amplify the interleukin-18 gene. Of the PCR products, the DNA fragment of about 500 bp was isolated and cloned into pBluescriptSK, and gene sequencing analysis and restriction enzyme treatment analysis confirmed that it was the murine interleukin-18 gene (GenBank accession number NM_E17139).

(2) Preparation of Murine Interleukin-18 Gene Containing Secretion Signal Sequence Murine interleukin-18 protein (GenBank accession number NP_032386) is cleaved by caspase-1 to generate an active form comprising the amino acids of from positions 36 (asparagine) to 192, with the removal of the amino acids of from positions 1 to 35 (aspartic acid). Hence, the mature interleukin-18 gene of SEQ ID NO:2, which is a murine interleukin-18 gene with the removal of a DNA portion corresponding to the peptide of positions 1 to 35 (a portion comprising the nucleotide sequence of positions 1 to 269 of GenBank accession number NM_008360), was linked to the extracellular secretion signal sequence of the positions 31~82 (SEQ ID NO:3) of the GM-CSF (GenBank accession number X03221) at its 5' terminal.

(3) Cloning of Human Interleukin-18 Gene

Human interleukin-18 (GenBank accession number NM_E17135) was cloned using SEQ ID NO:14 and SEQ ID NO:15 as primers, and a human liver cDNA library as a template.

(4) Preparation of Human Interleukin-18 Gene Mutant

As the human interleukin-18 proteins (GenBank accession number BAA08706) are inactivated by the cleavage by caspase-3, we attempted to prepare the mutant protein of SEQ ID NO:5 wherein aspartic acids at positions 71 and 76 are substituted by glutamic acid. Hence, a human interleukin-18 gene mutant comprising SEQ ID NO:6 was prepared by substituting the nucleotide sequence GAT corresponding to the positions 71 and 76 by GAG.

(5) Preparation of Human Interleukin-18 Gene Mutant Containing Secretion Signal Sequence As the human interleukin-18 protein mutants prepared in 4, wherein aspartic acids at positions 71 and 76 are substituted by glutamic acid, are activated by the removal of the amino acids of positions 1 to 36 (aspartic acid) by caspase-1, a signal sequence was linked to the upstream of the amino acid of position 37 by the same method as used in the linkage of mouse signal sequence. Hence, the mature interleukin-18 gene of SEQ ID NO:8, wherein a portion comprising the nucleotide sequence of the positions 1 to 285 of a DNA portion corresponding to the peptides of positions 1 to 36 of human interleukin-18 mutant gene (SEQ ID NO:6) is deleted, was linked to the extracellular secretion signal sequence (SEQ ID NO:16) of a preprotrypsin enzyme at the 5' terminal.

EXAMPLE 2

Construction of Recombinant Adenoviral Transfer Vector and Recombinant Virus (1) Construction of Recombinant Adenoviral Transfer Vector The murine interleukin-18 gene (GenBank accession number NM_E17139), the human interleukin-18 gene (GenBank accession number NM_E17135), the murine interleukin-18 gene containing the secretion signal sequence (SEQ ID NO:3+SEQ ID NO:2), the human interleukin-18 gene mutant (SEQ ID NO:6), and the human interleukin-18 gene containing the secretion signal sequence (SEQ ID NO:16+SEQ ID NO:8) were cloned into pcDNA3 (Invitrogen), respectively, and their protein expression was verified.

The murine interleukin-18 gene (GenBank accession number NM_E17139), the human interleukin-18 gene (GenBank accession number NM_E17135), the murine interleukin-18 gene containing the secretion signal sequence (SEQ ID NO:3+SEQ ID NO:2), the human interleukin-18 gene mutant, and the human interleukin-18 gene containing the secretion signal sequence (SEQ ID NO:16+SEQ ID NO:8) were cloned into pXCX2.dCMV, which is an adenoviral transfer vector (constructed in Dr. Dong-Soo, Im's lab at the Korea Research Institute of Bioscience and Biotechnology), to construct pX.dCMV.mIL-18, pX.dCMV.GMmIL-18, pX.dCMV.hIL-18, pX.dCMV.hIL-18CPP32-, and pX.preprotrypsin.hIL-18CPP32-, respectively (FIGS. 1a–1d).

(2) Construction of Recombinant Adenovirus

Figure 2:
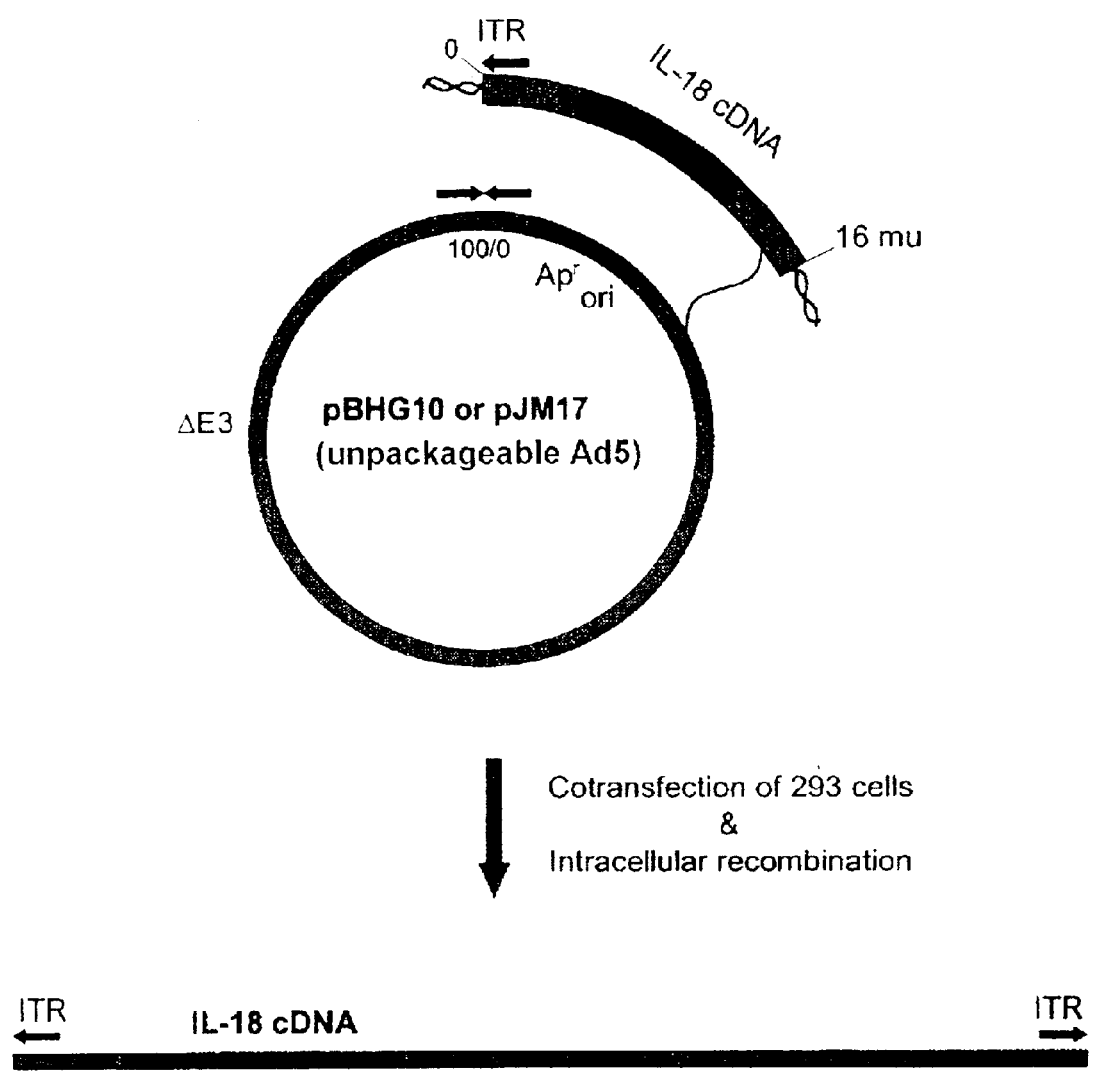
FIG. 2 shows a procedure for constructing recombinant adenoviruses using the adenoviral transfer vectors of the invention.

The four kinds of vectors, pX.dCMV.mIL-18, pX.dCMV.GMmIL-18, pX.dCMV.hIL-18, pX.dCMV.hIL-18CPP32-, and pX.preprotrypsin.hIL-18CPP32- were cotransfected into a 293 cell line together with pBHG10 (Microbix Biosystem Industry, Canada), which is an adenoviral parental vector, to allow the interleukin-18 gene to be introduced at the site of adenoviral E1 by a homologous recombination method (FIG. 2). The resulting recombinant viruses were designated as Ad.promIL-18, Ad.GMmIL-18, Ad.prohIL-18, Ad.hIL-18CPP32-, and Ad.preprotrypsin.hIL-18CPP32-, respectively, and Ad.GMmIL-18 was deposited at the KCTC (Korean Collection for Type Cultures) under KCTC10062BP.

The murine interleukin-18 gene (GenBank accession number NM_E17139), the human interleukin-18 gene (GenBank accession number NM_E17135), the murine interleukin-18 gene containing the secretion signal sequence (SEQ ID NO:3+SEQ ID NO:2), and the human interleukin-18 gene mutant inserted into Ad.promIL-18, Ad.GMmIL-18, Ad.prohIL-18, and Ad.hIL-18CPP32-, respectively, were confirmed by the restriction enzyme cleavage and PCR analysis.

(3) Proliferation of Adenovirus and Determination of Titer

To proliferate adenoviruses, a human 293 cell line was used. The human 293 cell line is a human embryonic kidney cell line containing the E1 gene of human adenovirus, and thus it can proliferate replication-defective recombinant adenoviruses. The 293 cells were cultured in a DMEM (Dulbecco's Modified Eagle Medium) medium containing 10% FBS.

The viruses of 5 MOI were mixed with 0.8 ml of serum-free DMEM, and then this virus solution was added to a 90% confluency of the 293 cells from which the culture medium was eliminated, and incubated for 1 hour at 37° C. for infection. During the incubation, the culture plates were inclined every 20 minutes for the virus culture medium to cover the cells evenly. After 1 hour, the virus infection solution was removed and a fresh culture medium was added. After culturing for 24–36 hours, a CPE (cytopathic effect) was observed. The CPE could be discerned by the phenomenon that cells became spherical and detached from the culture plate. After the CPE occurred, the medium was removed and the cells were scraped and collected in about 1–2 ml of FBS-containing DMEM medium. The cells were frozen and thawed at −70° C. and room temperature, respectively, three times. The supernatant collected by centrifugation was used to determine the virus titer. In general, about $10^6$ to $10^{10}$ virus particles were obtained from a 100 mm culture dish. The obtained viruses were used for experiments in this state, or stored at −20° C.

Virus titer was determined by plaque assay by using 60 mm culture plates. The virus stock was gradually diluted in serum-free media to the concentrations of $10^{-4}$, $10^{-5}$, $10^{-6}$, $10^{-7}$, $10^{-8}$, and $10^{-9}$. 0.4 ml of each diluted virus was infected to the 293 cells by the same method as described above, and 5 ml of serum-containing media including 1% gum was poured onto the cells in each plate and then incubated at 37° C. At 4–5 days after infection, the medium containing a gum was added once again. The plaque of the viruses appeared generally between 5 and 9 days to the extent that they could be visibly observed, and thus the titer could be determined.

EXAMPLE 3

Detection of Expression of Recombinant Interleukin-18

To detect the expression of proteins from the recombinant adenovirus, Hela, a human cervical carcinoma cell line, was used. Hela cells were cultured in a DMEM (Dulbecco's Modified Eagle Medium) containing 10% FBS.

Hela cells were cultured on the culture plate until they reached more than 90% confluency, and Ad.promIL-18, Ad.GMmIL-18, Ad.prohIL-18, Ad.hIL-18CPP32-, and control virus Ad.GFP were infected at 50 MOI, respectively, for 2 hours. They were incubated for 48 hours at 37° C. to allow the proteins to be sufficiently expressed.

To detect the expression of interleukin-18 proteins, the medium and the cells were separated by centrifugation. The secreted interleukin-18 was detected by immunoprecipitation. Gel slurry on which flag-antibody was immobilized was added to the culturing medium and reacted for 4 hours at 4° C., and gel was collected by centrifugation and washed in series with a bead washing solution (40 mM Hepes pH 7.4, 100 mM KCl, 0.1% NP-40, 0.1 mM DTT) and a PBS solution (10 mM sodium phosphate, 150 mM NaCl, pH 7.4). Then SDS-PAGE was performed and proteins were transferred onto a PVDF membrane. The membrane was reacted with a PBST (0.05% Twin 20 containing PBS) solution containing 10% skim milk, then washed, and reacted with mouse anti-flag antibody as a primary antibody. The membrane was reacted again with rabbit anti-mouse antibody conjugated with HRP (horseraddish peroxidase) which is a secondary antibody, washed with PBST, and then its color reaction was detected using an ECL kit (Amersham).

The cells were washed with PBS buffer, and then the cells were resuspended in RIPA solution (10 mM Tris-Cl, pH 8.2, 1% Triton X-100, 1% sodium deoxycolate, 0.1% SDS, 0.15 M NaCl, 0.02% sodium azide). The cells were disrupted by sonication and centrifuged to collect the supernatant. Aliquots of supernatants were applied to SDS-PAGE and immunoblotted by the same method as described above to detect the expression of interleukin-18 protein.

Figure 3:
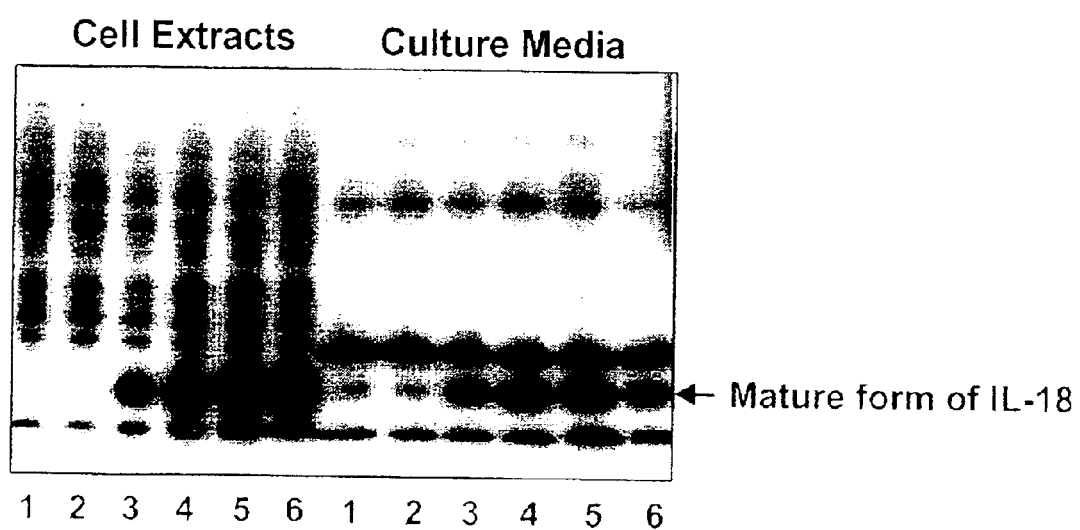
FIG. 3 is a western blot photograph showing the expression of recombinant interleukin-18 proteins by the recombinant adenoviruses of the invention.

FIG. 3 is a western blot photograph showing the expression of recombinant interleukin-18 proteins from the recombinant adenoviruses of the invention. In lanes 1 to 6, samples were obtained from the cell extracts, and in lanes 7 to 12, from media. Lanes 1 and 7 represent proteins expressed in the cells in which the viruses are not infected; lanes 2 and 8 represent control Ad.GFP; lanes 3 and 9 represent Ad.promIL-18; lanes 4 and 10 represent Ad.GMmIL-18; lanes 5 and 11 represent Ad.prohIL-18; and lanes 6 and 12 represent Ad.hIL-18CPP32-.

The mature interleukin-18 is 18 kDa. Interleukin-18 was not expressed in Ad.GFP viruses (Lane 2 in FIG. 3), and in other recombinant viruses, interleukin-18 was detected intracellularly and extracellularly. Also, Ad.GMmIL-18 possessing the GM-CSF signal sequence expressed a larger amount of proteins than Ad.promIL-18, and secreted them extracellularly.

EXAMPLE 4

Verification of Interferon Gamma Inducing Activity by Recombinant Interleukin-18 Proteins To verify if the recombinant interleukin-18 proteins maintain their original function as a cytokine, the induction of interferon gamma in mouse spleen cells (T cells) was tested.

Hela cells were infected with Ad.promIL-18, Ad.GMmIL-18, Ad.prohIL-18, Ad.hIL-18CPP32-, and control virus Ad.GFP, respectively, to obtain cell extracts and culture solution.

A spleen was excised from a mouse, and red blood cells and B cells were removed therefrom to incubate only T cells. 50 µl each of the cell extracts and culture solution were added to the resulting mouse spleen (T cells), which were cultured at 37° C. for 2 hours. The culture was centrifuged to obtain the supernatant.

The antibody against interferon gamma was reacted with the supernatant and the production of interferon gamma in spleen (T cells) was confirmed by the sandwich ELISA method (Genzyme). As a capture antibody, hamster (?) anti-mouse interferon gamma antibody was diluted in a capture buffer (carbonate buffer: 1.59 g of $Na_2CO_3$, 2.95 g of $NaHCO_3$, and 0.2 g of $NaN_3$, pH 9.6) at the concentration of 150 ng/ml and adhered onto the well, which was blocked with PBST containing 3% fatty acid-free BSA, and washed with PBS. The supernatants were added into each well and reacted for 1 hour at 37° C. Each well was washed again, and then biotin-conjugated anti-mouse interferon gamma, a secondary antibody, was added at 1 μg/ml and reacted for 1 hour at 37° C. Streptoavidin conjugated with HRP was added to each well, reacted, and washed. OPD (o-phenylene diamine) was mixed with phosphoric acid-citric acid buffer (0.1M citric acid, 0.2M $Na_2HPO_4$) together with $H_2O_2$, and added to each well to induce color reaction. The color reaction was terminated by the addition of 2M $H_2SO_4$, and then the absorbance was measured by an ELISA reader at a wavelength of 492 nm. For a standard curve showing the correlation of the absorbance and the quantity of interferon, the interferon gamma contained in the kit was used, and the quantity of interferon produced was determined.

FIG. 4 is a graph showing the quantity of interferon gamma produced by recombinant interleukin-18 proteins. "1" represents the amount of interferon gamma expressed in the cells without virus infection; "2" represents expression in cells infected with control Ad.GFP; "3" represents expression in cells infected with Ad.promIL-18; "4" represents expression in cells infected with Ad.GMmIL-18; "5" represents expression in cells infected with Ad.prohIL-18; and "6" represents expression in cells infected with Ad.hIL-18CPP32-. In FIG. 4, interleukin-18 proteins expressed from Ad.GMmIL-18 induced the largest amount of interferon gamma, and in particular, interleukin-18 proteins secreted to the medium exhibited the strongest interferon gamma induction.

EXAMPLE 5

Verification of Anticancer Effect of Ad.GMmIL-18 Against Kidney

Cancer Cell Line (Renca)

To verify the anticancer effect of interleukin-18, the Renca cell line, which is a mouse kidney cancer cell line, and the Huh-7 cell line, which is a human liver cancer cell line, were used. The Renca cell line was incubated in an RPMI medium containing 10% FBS, and the Huh-7 cell line was incubated in DMEM containing 10% FBS.

After the Renca cells were incubated in the RPMI medium containing 10% FBS, the cells were harvested and the number of cells were determined, and when it was found that the living cells constituted more than 80% of the total, they were washed with 1×PBS and resuspended in 1×PBS to $10^6$cells/ml. 100 μl ($10^5$ cells) of the resuspension were hypodermally injected at 100 μl per BALB/c mouse (cell number of $10^5$) to form a tumor nodule for 7–9 days.

15 Mice in which tumor nodules were formed were divided into three groups (five mice per group), and in the first group, the second group, and the control group (the third group), $1×10^9$ pfu/100 μl of Ad.promIL-18, Ad.GMmIL-18, and Ad.GFP, respectively, were injected into each nodule when the diameter of the tumor nodule was 5 mm. The recombinant viruses were diluted in a buffer for injection (10 mM Tris-HCl, pH 7.4, 1 mM $MgCl_2$), and the injection volume was 100 μl per mouse. The size of each tumor was calculated by length×width×height/2 and an average value was taken.

FIG. 5 is a graph showing the change in tumor size according to time after Ad.promIL-18, Ad.GMmIL-18, and Ad.GFP were injected into the mice in which the tumor nodules were formed. In FIG. 5, the size of tumors into which the viruses (Ad.promIL-18, Ad.GMmIL-18) expressing interleukin-18 were introduced was reduced remarkably in comparison with the control (Ad.GFP: ▲), and Ad.GMmIL-18 (●) expressing the interleukin-18 proteins extracellularly exhibited the greatest inhibiting effect against tumor proliferation.

To examine whether the anticancer efficiency of Ad.GMmIL-18 is statistically significant, 40 mice having mouse kidney cancer were divided into two groups, and Ad.GMmIL-18 and Ad.GFP (control) were respectively injected into tumor nodules of the two groups. The disappearance and proliferation of the tumors were then examined for 21 days (Table 1). The anticancer efficiency was classified into three categories: 1) complete regression, in a case that the tumor completely disappeared; 2) partial regression, in a case that the proliferation of the tumor was remarkably reduced or tumor hardly proliferated; and 3) nonresponse, in a case that the proliferation did not show any difference in comparison with the control. The significance of anticancer efficiency was verified by a Student's test, and the case wherein the P value was not more than 0.05 was regarded as significant.

TABLE 1

| | Response (%) | | |
|---|---|---|---|
| Treatment | Complete regression | Partial regression | Nonresponse |
| Ad.GMmIL-18 (1 × $10^9$ pfu) | 4/20 (20) | 8/20 (40) | 8/20 (40) |
| Ad.GFP (1 × $10^9$ pfu) | 0/20 (0) | 4/20 (20) | 16/20 (80) |

In the control, partial regression was observed in 4 of 20 mice and the inhibition efficiency against tumor proliferation was 20%, whereas in the Ad.GMmIL-18-treated group, partial regression was observed in 8 and complete regression was observed in 4 of 20 mice, and the inhibition efficiency against tumor proliferation by Ad.GMmIL-18 was 60%. In a test to examine whether the inhibition efficiency against tumor proliferation by Ad.GMmIL-18 was statistically significant in comparison with the control, the P value for the complete regression was found to be 0.035, and P value for both the complete regression and partial regression was found to be 0.0098. This result suggests that the inhibition efficiency against tumor proliferation by Ad.GMmIL-18 is statistically significant.

EXAMPLE 6

Verification of Anticancer Effect of Ad.hIL-18CPP32- Against Liver Cancer Cell Line (Huh-7)

An Huh-7 mouse liver cancer cells were hypodermically injected into 30 BALB/c-nude mice to form tumor nodules, which were allowed to grow until their diameter reached 4–5 mm. The mice were divided into three groups (10 mice in each group), and Ad.hIL-18CPP32-+Ad.ICE, Ad.ICE, and Ad.GFP were used for each group, respectively. The recombinant viruses were injected into the tumor nodules, and the change in the size of tumor nodules was measured.

FIG. 6 is a graph showing the size of tumor nodules after the injection of recombinant viruses into mice wherein the tumor nodule was formed by liver cancer cells. Co-treatment with Ad.hIL-18CPP32- and Ad.ICE (●exhibited the highest inhibition effect against tumor growth.

In a comparison analysis to examine whether the inhibition efficiency against tumor proliferation by the treatment of Ad.hIL-18CPP32-+Ad.ICE is statistically significant in comparison with Ad.GFP (control), the P value was found to be 0.0098. This result suggests that the inhibition efficiency against tumor growth by Ad.hIL-18CPP32-+Ad.ICE is statistically significant.

TABLE 2

| Treatment | Response (%) | | |
| --- | --- | --- | --- |
| | Complete regression | Partial regression | Nonresponse |
| Ad.hIL-18CPP32- + Ad.ICE (5 × 10⁸ pfu + 5 × 10⁸ pfu) | 2/10 (20) | 3/10 (30) | 5/10 (50) |
| Ad.ICE (1 × 10⁹ pfu) | 0/10 (0) | 1/10 (10) | 9/10 (90) |
| Ad.GFP (1 × 10⁹ pfu) | 0/10 (0) | 0/10 (0) | 10/10 (100) |

Two of ten mice exhibited complete regression of the tumor nodule, and three mice exhibited partial regression. Therefore, the inhibition efficiency against tumor proliferation was 50% in Ad.hIL-18CPP32-+Ad.ICE, and 10% in control Ad.ICE (Table 2).

EXAMPLE 7

Verification of Cytotoxic Lymphocytes Inducing Ability

Ad.GMmIL-18 and Ad.GFP were each injected into tumor nodules formed hypodermally in mice. After 21 days, the spleen cells of the mice in which the tumor proliferation was inhibited were excised and made a single cell suspension by metal mesh through aseptic manipulation, and then red blood cells were dissolved (8.3 g/L ammonium chloride). The spleen cells were resuspended in a T cell medium (RPMI, Eagle-Hanks amino acid, FBS, L-glutamin, beta-mercaptoethanol, penicillin-streptomycin) and added to 12 wells at 1×10⁷ cells per well. Renca cells were treated with trypsin-EDTA and incubated with 50 µg/ml of mitomycin C for 20 minutes at 37° C. After washing with the medium 3–4 times, the Renca cells were resuspended in the T cell medium and added to and incubated in wells in a ratio of 10:1 with spleen cells. After 3–4 days, the stimulated T cells (effector cells) were mixed with $^{51}$Cr(100 Ci/10⁶ cells; Dupont)-labeled Renca cells (target cells) in 11:1, 33:1, and 100:1 ratios in 96 U-shaped bottom well plates so that the final volume was 200 µl. They were incubated for 3–4 hours at 37° C. and the culture solution was centrifuged. 100 µl of supernatant was taken and measured by a gamma counter to calculate the percentage of cell lysis (% specific lysis).

FIG. 7 is a graph showing the percentage of cell lysis which represents the production of CTL (Cytotoxic T Lymphocyte) activated by Ad.GMmIL-18 or Ad.GFP. It is shown that in mice treated with Ad.GMmIL-18, cancer cell specific cytotoxic lymphocytes were induced (CTL production).

EXAMPLE 8

Verification of Natural Killer (NK) Cell Activity Promoting Ability

Ad.GMmIL-18, Ad.hIL-18CPP32-, Ad.GFP, and Ad.ICE were each injected into tumor nodules in mice. After three weeks, the spleen cells from mice in which the tumors were inhibited were made a single cell suspension, and then the spleen cells were resuspended in T cell medium to be used as a stimulated T cell (effector T cell). The stimulated T cells were mixed with $^{51}$Cr(100 µ Ci/10⁶ cells; Dupont)-labeled (90 min) YAC-1 cells (target cells) in 96 U-shaped bottom plates in 11:1, 33:1, and 100:1 ratios, respectively, so that the final volume was 200 µl, and then incubated for 3–4 hours at 37° C. The culture medium was centrifuged and 100 µl of supernatant was taken and measured by a gamma counter to calculate the percentage of cell lysis (% specific lysis). As a result, it was observed that in mice treated with the adenoviruses comprising interleukin-18, the activity of NK cells was remarkably increased (FIG. 8).

The recombinant adenoviruses expressing interleukin-18 in the invention promote the activity of immune cells, thereby exhibiting excellent effects in killing cancer cells or inhibiting their growth. Accordingly, the adenoviruses of the invention can be used for gene therapy to boost immunity and treat cancers.

What is claimed is:

1. A recombinant adenovirus comprising
   (a) a promoter operably linked to a gene so that the gene can be expressed, wherein the gene encodes a human interleukin-18 protein mutant in which a caspase-3 cleavage site is modified; and
   (b) a polyadenylation signal sequence operably linked to the gene.

2. The recombinant adenovirus according to claim 1, wherein an amino acid of the caspase-3 cleavage site at position 71 and/or 76 of the human intereukin-18 protein mutant is selected from the group consisting of alanine, arginine, asparagine, cysteine, glutamine, glutamic acid, glycine, histidine, isoleucine, leucine, lysine, methionine, phenylalanine, proline, serine, threonine, tryptophan, tyrosine, and valine.

3. The recombinant adenovirus according to claim 1 wherein the human interleukin-18 protein mutant is a mutant of interleukin-18 precursor or a mutant of mature inteleukin-18.

4. The recombinant adenovirus according to claim 2, wherein the human interleukin-18 protein mutant comprises the polypeptide of SEQ ID NO:4 or the polypeptide of SEQ ID NO:10.

5. The recombinant adenovirus according to claim 1, wherein the gene comprises the nucleotide sequence of SEQ ID NO:6 or the nucleotide sequence of SEQ ID NO: 8.

6. The recombinant adenovirus according to claim 1, wherein the gene further comprises a signal sequence for extracellular secretion.

7. The recombinant adenovirus according to claim 6, wherein the signal sequence for extracellular secretion comprises the nucleotide sequence of SEQ ID NO:3 or signal sequence of SEQ ID NO:16.

8. A recombinant adenovirus comprising:
   (a) a promoter operably linked to an interleukin-18 gene so that the interleukin-18 gene can be expressed, wherein the interleukin-18 gene comprises a nucleotide sequence encoding a human interleukin-18 protein wherein an amino acid of a caspase-3 cleavage site of the human interleukin-18 protein is substituted by an amino acid selected from the group consisting of alanine, arginine, asparagine, cysteine, glutamine, glutamic acid, glycine, histidine, isoleucine, leucine, lysine, methionine, phenylalanine, proline, serine, threonine, tryptophan, tyrosine, and valine; and (b) a polyadenylation signal sequence operably linked to the interleukin-18 gene.

9. A recombinant adenovirus comprising:

(a) a promoter operably linked to an interleukin-18 gene so that the interleukin-18 gene can be expressed, wherein the interleukin-18 gene comprises a nucleotide sequence encoding a human interleukin-18 protein wherein an amino acid of a caspase-3 cleavage site of the human interleukin-18 protein is substituted by an amino acid selected from the group consisting of alanine, arginine, asparagine, cysteine, glutamine, glutamic acid, glycine, histidine, isoleucine, leucine, lysine, methionine, phenylalanine, proline, serine, threonine, tryptophan, tyrosine, and valine; and (b) a polyadenylation signal sequence operably linked to the interleukin-18 gene; wherein the human interleukin-18 protein is selected from the group consisting of mutants of the wild-type mature interleukin-18 protein and mutants of the wild-type interleukin-18 precursor.

10. The recombinant adenovirus according to claim 8, wherein the amino acid of the caspase-3 cleavage site is at position 71 and/or position 76 of the human interleukin-18 protein.

11. The recombinant adenovirus according to claim 8, wherein the amino acid of the caspase-3 cleavage site of the human interleukin-18 protein is substituted by glutamic acid.

12. The recombinant adenovirus according to claim 8, wherein the interleukin-18 gene encodes a mature human interleukin-18 protein and a signal sequence for extracellular secretion.

13. The recombinant adenovirus according to claim 12, wherein the signal sequence for extracellular secretion comprises nucleotide sequence of SEQ ID NO:3 or signal sequence of SEQ ID NO:16.

* * * * *